United States Patent [19]

Kramer et al.

[11] Patent Number: 5,062,774
[45] Date of Patent: Nov. 5, 1991

[54] SOLUTION PUMPING SYSTEM INCLUDING DISPOSABLE PUMP CASSETTE

[75] Inventors: David E. Kramer, Northbrook; Andrew J. Muetterties, Mundelein; Walter T. Szempruch, Gurnee, all of Ill.

[73] Assignee: Abbott Laboratories, Abbott Park, Ill.

[21] Appl. No.: 444,459

[22] Filed: Dec. 1, 1989

[51] Int. Cl.$^5$ .............................................. F04B 43/04
[52] U.S. Cl. ..................... 417/413; 417/435; 417/479; 417/503; 128/DIG. 12
[58] Field of Search ............... 417/395, 413, 434, 435, 417/479, 502, 503; 604/80, 81, 153; 128/DIG. 12

[56] References Cited

U.S. PATENT DOCUMENTS

| | | | |
|---|---|---|---|
| 4,236,880 | 12/1980 | Archibald | 417/479 X |
| 4,303,376 | 12/1981 | Siekmann | 417/395 X |
| 4,479,761 | 10/1984 | Bilstad et al. | 417/479 X |
| 4,818,186 | 4/1989 | Pastrone et al. | 417/413 X |
| 4,842,584 | 6/1989 | Pastrone | 604/153 X |

Primary Examiner—Richard A. Bertsch
Assistant Examiner—Eugene L. Szczecin, Jr.
Attorney, Agent, or Firm—A. Nicholas Trausch

[57] ABSTRACT

A solution pumping system including a disposable pump cassette is disclosed, with the system configured for efficient and accurate preparation of parenteral admixture solutions. The system includes a pump driver having a reciprocable pump plunger and a plurality of associated valve actuators. The disposable pump cassette of the system is configured for removable positioning in operative association with the pump driver, and includes a positive displacement pump configured for operation by the reciprocable pump plunger. The pump cassette further includes a plurality of liquid inlets, and at least one liquid outlet joined in fluid communication with the inlets. By selective operation of the valve actuators of the pump driver, one or more selected source solutions are drawn through the pump inlets by the positive displacement pump, and directed through the pump outlet to an admixture solution container. Preferred features of the present pump cassette facilitate liquid flushing to avoid mixture of incompatible source solutions, and enhance the sealing integrity of the cassette construction.

22 Claims, 7 Drawing Sheets

SOLUTION PUMPING SYSTEM INCLUDING DISPOSABLE PUMP CASSETTE

TECHNICAL FIELD

The present invention generally relates to solution pumping systems for preparation and administration of patient parenteral solutions, and more particularly to a solution pumping system including a disposable pump cassette configured for efficient and accurate compounding of parenteral solutions, and other applications requiring delivery of multiple reagents or therapeutic agents to a common delivery point.

BACKGROUND OF THE INVENTION

Modern patient care in a hospital or other health care facility requires the preparation and intravenous or intramuscular administration of very large numbers of parenteral solutions to patients. Such solutions include those for both nutritional purposes, as well as drug-containing therapeutic solutions.

In view of the very large numbers of such solutions which must be handled on a daily basis in a health care facility, efficient and accurate preparation and administration of such solutions is highly desirable. To this end, one very significant advancement in recent years has been the development of positive displacement fluid infusion pumping devices for intravenous or intramuscular administration of solutions to patients. Such systems have, in large measure, replaced the previously employed gravity flow control systems, primarily due to their much greater accuracy in delivery rates and dosages, and their relative sophistication in permitting flexible and controlled feed from multiple liquid sources. In particular, such infusion pumping devices permit precise control of drug administration to a patient over a given period of time.

U.S. Pat. No. 4,639,245, to Pastrone et al., U.S. Pat. No. 4,818,186, to Pastrone et al., and U.S. Pat. No. 4,842,584, to Pastrone, all of which are hereby incorporated by reference, disclose a positive displacement fluid infusion pumping device and components thereof which has met with widespread acceptance by the patient care field. This pumping system includes the combination of a pump driver and an associated removable and disposable pump cassette. The pump cassette includes a self-contained positive displacement pump device, which is operated in the desired manner by a reciprocable pump plunger of the associated pump driver. The pump driver further includes selectively operable valve actuators, which actuators cooperate with a plurality of valve mechanisms provided in the pump cassette, with the system thus providing accurate and highly automated administration and infusion of parenteral solution.

The present invention is directed to a solution pumping system including a disposable pump cassette which will permit the same highly-desirable efficiency, accuracy, and automation in the compounding and preparation of such parenteral solutions. While the present system is particularly suited for preparation of so-called small volume parenteral solutions, typically including drugs or other therapeutic agents for administration to patients, the principles disclosed herein are equally suitable for a system for preparation of large volume parenterals, typically comprising nutritional solutions for patients, as well as for use with other applications requiring compounding of multiple reagents or therapeutic agents.

At present, the pharmacies at hospitals and other health care facilities typically admix small volume parenteral solutions manually The pharmacist selects an intravenous solution container, typically a bag, that is either partially empty, or that contains the appropriate base nutritional solutions or diluents. The pharmacist or assisting personnel then calculates the amounts of the various liquid components that need to be added to the solution container in accordance with the physician's order. These components are then measured by drawing them into syringes of the appropriate sizes. The contents of the syringes are then injected into the final solution container.

As will be appreciated, accurate preparation of parenteral solutions in this manner is time consuming, typically taking on the order of 20-30 minutes per physician order, assuming about 10 minutes of preparation time per bag when making three bags with six solution additions per bag. While appropriate protocols are established and followed for accuracy and consistency, the manual nature of the procedure does not preclude the possibility of errors in the preparation of the resultant admixtures. Additionally, the repeated needle-puncturing and additions of solutions to the admixture container increase the risk of contamination.

The present solution pumping system, including a disposable pump cassette, is particularly configured to facilitate accurate and efficient compounding of parenteral admixture solutions with minimal labor and a risk of contamination, particularly those of a relatively small volume containing drugs and like therapeutic agents, by eliminating manual addition of different source solutions, with the system lending itself for use with automated and programmable controls for further enhancing accuracy and efficiency.

SUMMARY OF THE INVENTION

The present solution pumping system, including a disposable pump cassette, has been particularly configured for efficient and accurate admixture of source solutions, particularly the preparation of small volume parenteral solutions. Notably, the system is arranged such that all source solutions and resultant admixtures flow through and only contact the disposable pump cassette (and associated fluid handling tubing and containers) of the system. As will be described, the pump cassette has been particularly configured to avoid undesirable mixture of incompatible solutions, as well as for precise and consistent pump operation. The pump cassette has further been configured to enhance seal integrity and ease of use.

The present system is essentially two-part in nature, including a pump driver, and a removable and disposable pump cassette. The pump driver, which is preferably provided with suitable automatic and programmable controls, includes a pump driver in the form of a reciprocable pump plunger, and a plurality of valve actuators, which are preferably solenoid-operated. For compounding parenteral solutions, the pump driver is ordinarily positioned in the pharmacy of a health care facility, typically in a laminar flow hood to abate contamination.

The pump cassette of the system interfaces with the pump driver, and provides the actual pump and valve mechanisms which permit compounding of plural source solutions for preparation of parenteral admixture solutions. The pump cassette includes a rigid cassette body comprising a plate-like front body member and a juxtaposed plate-like rear body member. The cassette further includes a membrane-like elastomeric diaphragm positioned in the cassette body between the front and rear body members.

The cassette body and the diaphragm function in the nature of a manifold and together provide the pump cassette with a plurality of liquid inlets, at least one liquid outlet, and a liquid flow path for joining the liquid inlets and outlet in fluid communication. The diaphragm cooperates with the cassette body to provide a valve mechanism at each of the various inlets and at the outlet of the cassette. In the preferred embodiment illustrated herein, the front body member of the cassette body defines the liquid inlets, outlet, and flow path, together with the associated diaphragm. The rear body member cooperates with the diaphragm and the front body member to hold the diaphragm in sealing engagement with the front body member. The rear body member defines a plurality of openings for engagement of the diaphragm by the pump plunger, and for engagement of the valve actuators of the pump driver with the valve mechanisms of the cassette.

The pump cassette further includes a positive displacement liquid pump which is operatively driven by the pump plunger of the pump driver, and which pumps liquid from a selected one of the liquid inlets to the liquid outlet via the flow path of the cassette. In the preferred form, the pump comprises a pump chamber which is defined by the front body portion of the cassette body, and a portion of the cassette diaphragm juxtaposed to the pump chamber.

Liquid flow is effected by reciprocation of the pump plunger against the diaphragm, in timed liquid outlet). The pump cassette may optionally include selectively operable pump inlet and outlet mechanisms for directing flow through the positive displacement pump.

Notably, the present pump cassette is particularly configured so as to lend itself for use in preparation of small volume parenteral admixtures, wherein the possibility exists for incompatible source solutions to be handled by the cassette. Specifically, during preparation of small volume parenteral admixtures, the source solutions used in preparing the admixture, such as drugs and like therapeutic agents, are introduced into the pump cassette in relatively high concentrations. Since some source solutions may be incompatible, undesirably forming precipitates at the concentrations at which they are employed for subsequent admixture, it is highly desirable to avoid mixture of such potentially incompatible source solutions.

To this end, at least one, and preferably a plurality of the downstream liquid inlets of the pump cassette are provided with a liquid flushing arrangement so that liquid flow between upstream and downstream portions of the flow path at the inlet flushes residual liquid from the region of the inlet, thereby avoiding mixture of concentrated incompatible liquids in the cassette by minimizing any stagnant area in the flow path. This liquid flushing arrangement is provided by the provision of at least one bypass passage of the cassette's flow path, which passage extends adjacent to a peripheral valve seat defined by the cassette body at the liquid inlet. In the illustrated embodiment, a pair of such bypass passages are provided extending on respective opposite sides of the peripheral valve seat streamlining lands for streamlining liquid flow past the valve seat. As will be appreciated, the preferred configuration essentially positions the liquid inlets directly in the flow path to effect the desired flushing action.

Further features of the present construction facilitate accurate and efficient use. The preferred embodiment is configured such that the liquid pump of the pump cassette is provided by a pump chamber defined by the front body member, and the associated portion of the cassette diaphragm. The front body member further preferably comprises an arrangement for positioning the cassette within the associated pump driver. Specifically, the cassette body defines at least one positioning opening within which a cassette positioning member of the pump driver is received. The front body member comprises the peripheral surface of the positioning opening, and thus is configured for engagement with the positioning member of the pump driver. By this arrangement, the front body member, defining the pump chamber and the various valve seats, is very accurately positioned with respect to the reciprocable pump plunger of the pump driver, thus facilitating highly accurate volumetric flow through the positive displacement pump, and precise valve operation. Such accurate flow is further facilitated by the provision of a double clamping rib arrangement at respective opposite sides of the cassette diaphragm at the pump, thus enhancing retention of the diaphragm attendant to deformation by the pump plunger for positive displacement pumping. welding. To this end, the front and rear body members of the cassette are joined to each other at a marginal joint extending along at least a portion of the confronting marginal edges of the body members. Notably, the front and rear body members are further joined together inwardly of the marginal joint at a diaphragm joint. The diaphragm joint extends completely about the periphery of the cassette diaphragm, thus enhancing the sealing of the liquid flow path of the cassette. By completely encapsulating and enclosing the diaphragm, the quantity of relatively expensive elastomer employed for molding the diaphragm is desirably decreased, since the diaphragm need not extend all the way to the confronting marginal edges of the front and rear body members.

Numerous other features and advantages of the present invention will become readily apparent from the following detailed description, the accompanying drawings, and the appended claims.

DETAILED DESCRIPTION

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated.

With reference now to the drawings, therein is illustrated a solution pumping system embodying the principles of the present invention. In the illustrated embodiment, the present system has been particularly configured for compounding of parenteral admixture solutions for intravenous or intramuscular administration to patients. For use in this manner, the present system is supplied through tubing S with a plurality of source solutions from associated containers C, which solutions are compounded, in accordance with a physician's order, to form an admixture solution in an admixture container A for subsequent patient administration. However, as will be appreciated, a solution pumping system, including a disposable pump cassette, embodying the principles of the present invention can be used for other applications wherein it is desirable to deliver a plurality of different source solutions to a single delivery point such as a suitable container.

In accordance with the present invention, the pumping system includes a disposable pump cassette 10 which is driven by, and can be removably received within, a pump driver 12. As will be further described, the pump cassette 10, together with its associated tubing (typically referred to as a disposable "set"), are the only portions of the present system with which the various source solutions and resultant admixtures come in contact. As such, the pump cassette and tubing are intended for periodic disposal (such as on a daily basis).

The present pump cassette is of a configuration to facilitate its efficient manufacture, but at the same time includes a number of structural features which lend to accurate, efficient, and reliable use of the present system. In a preferred embodiment, the pump cassette comprises a rigid, generally rectangular cassette body is preferably formed from rigid thermoplastic material, such as polycarbonate.

The pump cassette further includes a deformable elastomeric diaphragm 20 positioned between the front and rear body members. Diaphragm 20 cooperates with the cassette body 14, and in particular the front body member 16, to define and provide a plurality of liquid inlets, at least one liquid outlet, and a liquid flow path joining the inlets and outlet in fluid communication. The diaphragm cooperates with the front body member 16 to provide a selectively operable valve mechanism at each of the various liquid inlets and at the liquid outlet.

To this end, the face of the diaphragm 20 confronting the front body member 16 includes a raised positioning rib 20' extending continuously along the marginal edge portion of this diaphragm face. The positioning rib is held in position by associated wall portions 16' and 18' of the cassette body (see FIGS. 6 and 7), with the diaphragm maintained in sealing engagement against the front body member 16, by the securement of the rear body member 18 to the front body member in tightly fitting relationship against the rear face of the diaphragm 20. The diaphragm 20 also cooperates with the front body member 16 of the cassette body to provide a positive displacement liquid pump for pumping liquid from a selected one of the liquid inlets to the liquid outlet via the liquid flow path, as will be further described.

In order to ensure the integrity of the pump cassette construction, the plate-like front and rear body members 16 and 18 are preferably joined to each other in a substantially permanent manner. To this end, a marginal joint seal 19 is provided which extends along at least a portion of the confronting marginal edges of the rear body members. Preferably, a plurality of the marginal seals 19 (FIG. 4) are provided along both opposed pairs of marginal edges of the generally rectangular cassette body.

Figure 4:
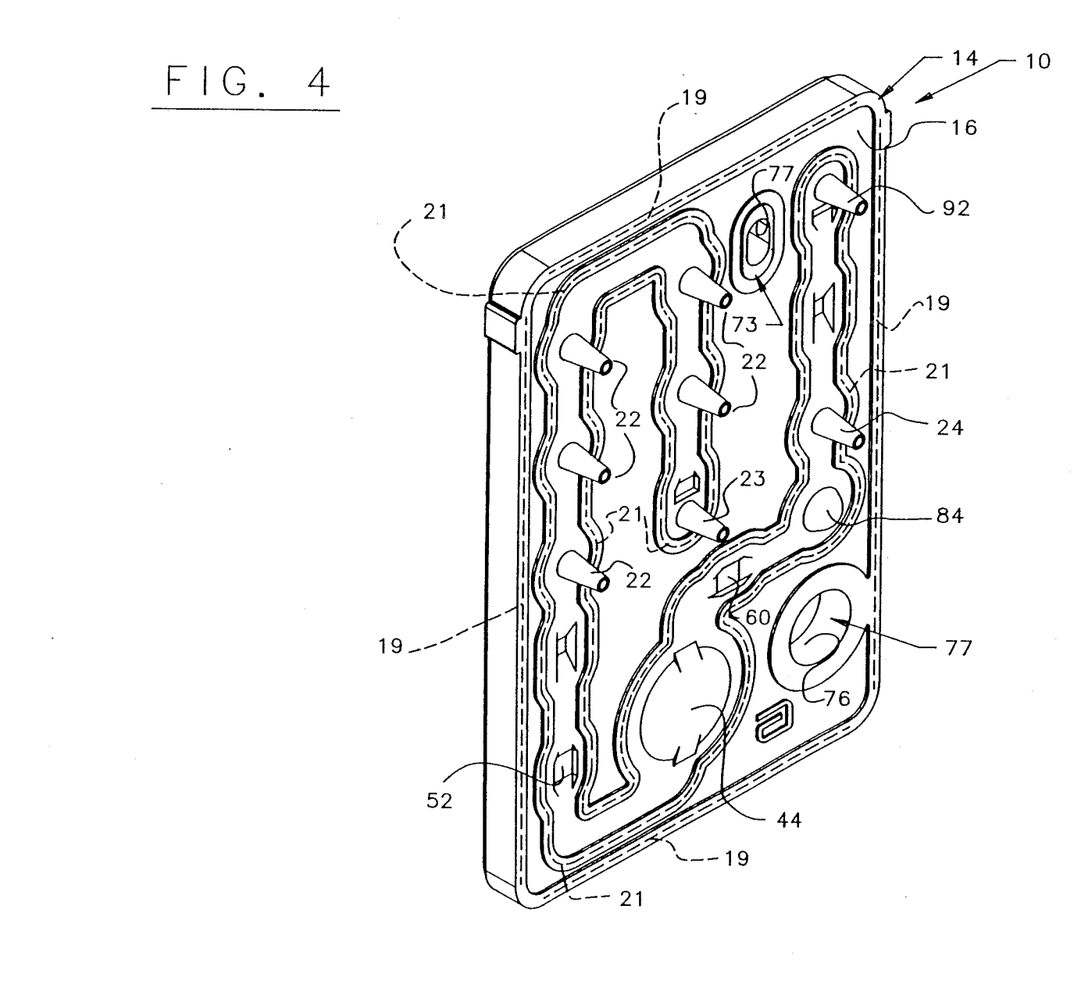
FIG. 4 is a front perspective view of the pump cassette of the present system.

Notably, the front and rear body members are further preferably joined to each other at a diaphragm joint seal 21 (FIG. 4). In order to enhance the sealing integrity of the cassette, and prevent any liquid flow outside of the intended flow path of the cassette, diaphragm joint seal 21 extends continuously and completely about the entire periphery of the cassette diaphragm 20 where rear body member wall portions 18' abut the front body member 16. Diaphragm joint seal 21 also preferably comprises sonic welding, and extends along and adjacent to the diaphragm 20 (note the preferred provision of sonic welding energy concentration walls 21', shown in FIGS. 6 and 7). By the resultant structure, all liquid flow within the cassette takes place between the front body member 16 and the diaphragm, with the rear body member 18 holding the diaphragm in tightly fitting and confronting relation to the front body member. As illustrated, the rear body member 18 defines a plurality of openings at which the diaphragm can be engaged for effecting liquid pumping and flow control within the cassette.

Figure 3:
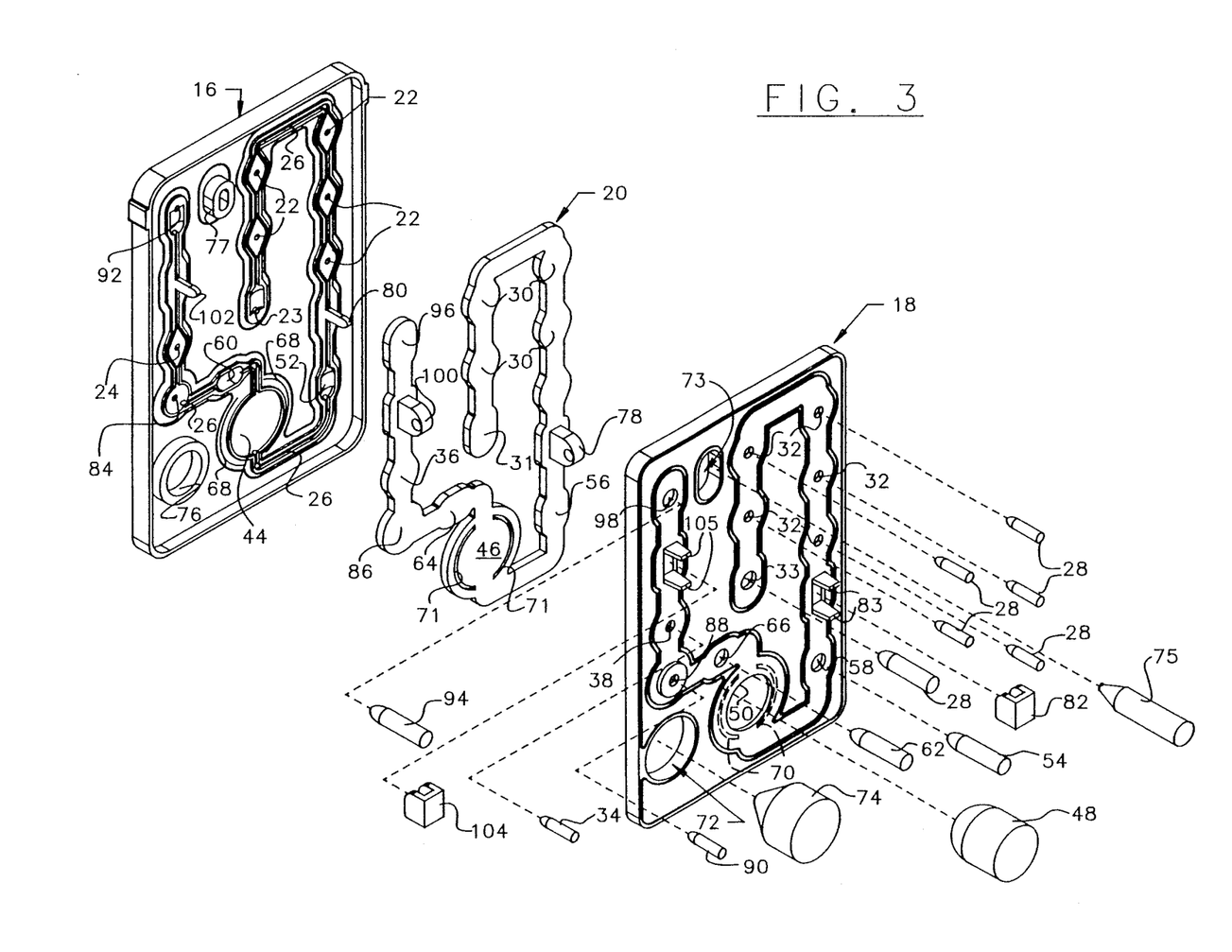
FIG. 3 is an exploded perspective view of a disposable pump cassette of the present system illustrated, in diagrammatic form, in operative association with a pump driver of the present system.
Figure 5:
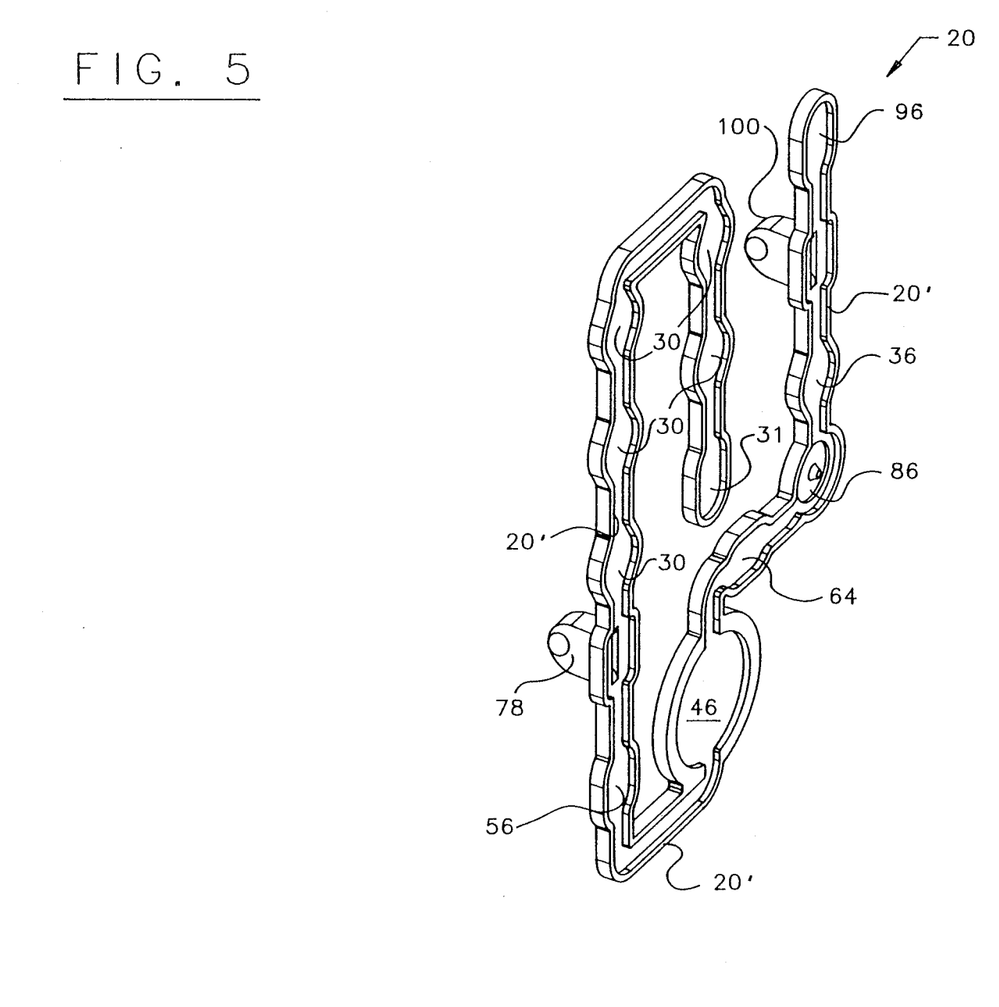
FIG. 5 is a perspective view of a diagram of the pump cassette shown in FIGS. 3 and 4.

With further reference to FIGS. 3-5, front body member 16 of the pump cassette defines, together with the diaphragm 20, a plurality of liquid inlets 22, an upstream most liquid inlet 23, at least one liquid outlet 24, and a liquid flow path 26 which joins the inlets and outlet in fluid communication. In the illustrated preferred form, the liquid flow path 26 includes a generally U-shaped portion having a pair of legs, with each of the legs having a plurality (three being illustrated) of the liquid inlets 22 and 23 positioned therealong.

Figure 1:
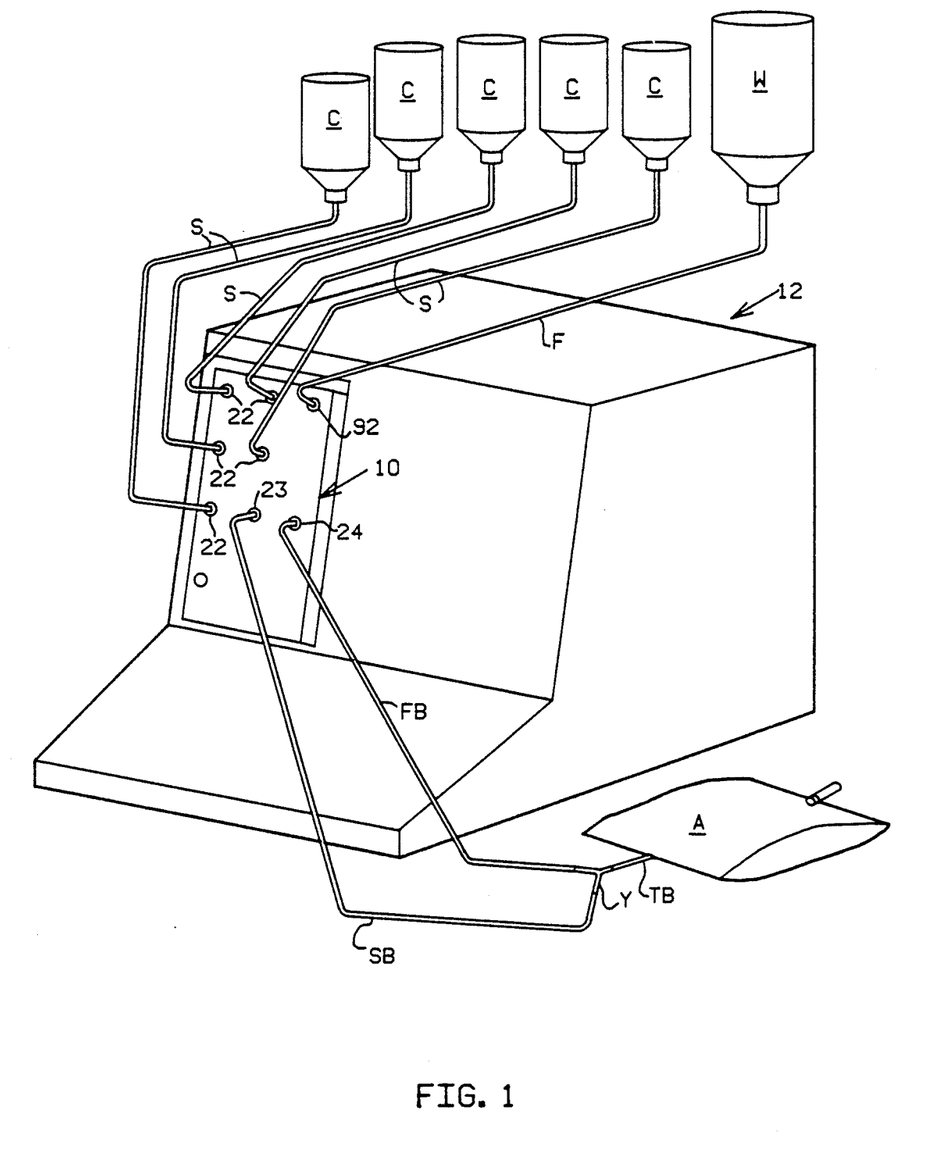
FIG. 1 is a diagrammatic perspective view of a solution pumping system, embodied as a compounding system for parenteral solutions, embodying the principles of the present invention.
Figure 2:
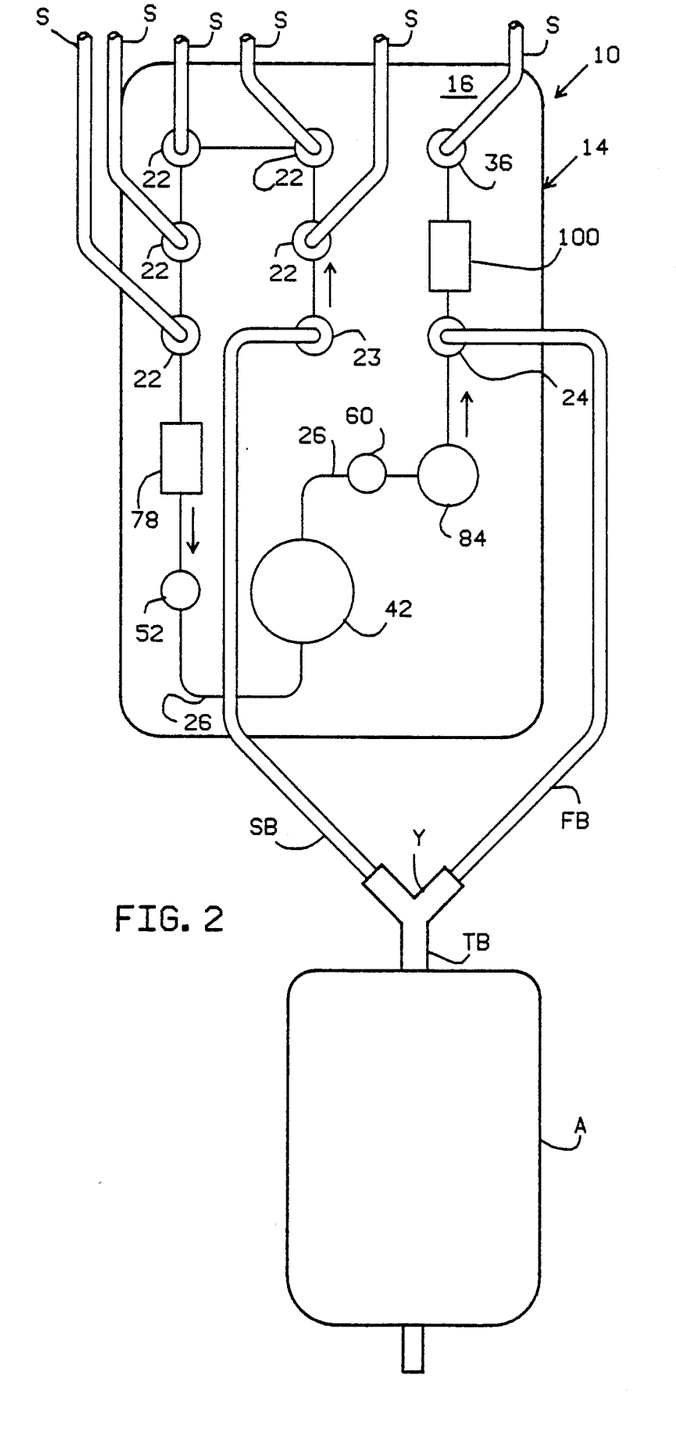
FIG. 2 is a diagrammatic view illustrating a pump cassette of the present system with an associated admixture container.

As illustrated in FIGS. 1 and 2, a Y-set tubing assembly joins the cassette in fluid communication with admixture container A. The tubing assembly includes a first branch FB joined to outlet 24, a second branch SB joined to inlet 23, and a third branch TB joined to the first and second branches, via Y-connector Y, and to container A.

In accordance with the present invention, and as will be further described hereinafter, each of the liquid inlets 22 includes an inlet passage defined by the front body member 16 of the cassette body, with the inlet passage terminating in a peripheral valve seat. At the inlet 23, an inlet passage 25 terminates at a valve seat 27 positioned adjacent to the inlet passage (see FIG. 6). In order to configure each inlet for respectively operatively engaging and deforming inlet diaphragm portions 30 at each liquid inlet 22, and a diaphragm portion 31 at inlet 23. Each of inlet valve actuators 28 preferably comprises a solenoid-actuated arrangement for reciprocating the actuator, thereby controlling liquid flow through a respective liquid inlet 22, 23. In a particularly preferred embodiment, and as disclosed in copending U.S. patent application Ser. No. 07/444,487, filed Dec. 1, 1989, a solenoid-operated valve actuator is employed, which actuator is configured to provide the desired closing force while avoiding excessive stress of the diaphragm 20. It is preferred that the solenoid of the valve actuator employed in the present system be configured for closing (under the influence of a return spring) in the event of power failure. As illustrated, each of the valve actuators 28 acts against the respective diaphragm portion 30 through an inlet actuator opening 32 defined by rear body member 18 of the pump cassette. The valve actuator 28 for the inlet 23 acts against diaphragm portion 31 through an inlet actuator opening 33.

A similar valve and actuating arrangement is provided in connection with liquid outlet 24. Specifically, pump driver 12 includes an outlet valve actuator 34 which operates against an outlet diaphragm portion 36, with the actuator engaging this diaphragm portion through an outlet valve opening 38 defined by the rear body member 18.

In keeping with the fundamental concept of the present system that all liquid flow through the system is only through the pump cassette 10, the pump cassette further includes a positive displacement liquid pump 42. The pump 42 includes a pump chamber 44 which is defined by front body member 16 of the cassette body, and further includes a confronting portion 46 of the diaphragm 20, which cooperates with the pump chamber 44 for effecting flow of liquid within the flow path of the pump cassette in the direction indicated by the arrows shown in FIG. 2. This is achieved by deformation and relaxation of the diaphragm portion 46 by a reciprocable pump plunger 48 of the associated pump driver 12. The pump plunger 48 acts against the diaphragm portion 46 through a plunger opening 50 defined by rear body member 18.

Control of liquid flow into and out of the pump chamber 44 is preferably effected by alternately opening and closing a selected upstream valve mechanism (such as at one of the inlets 22), and a selected downstream valve mechanism (such as at outlet 24). If desired, operatively associated pump inlet and outlet valves may optionally be provided Specifically, the front body member 16 of the pump cassette defines a pump inlet 52, which inlet can be operated by an optional inlet actuator 54 of the pump driver acting against a pump inlet diaphragm portion 56 via pump inlet opening 58. Similarly, a pump outlet 60 can be provided by the front body member 16, with an optional pump outlet actuator 62 of the pump driver acting against a pump outlet diaphragm portion 64 through an outlet opening 66. When flow control through the pump is effected in the preferred fashion by operation of a selected inlet 22, 23 and the outlet 24, the pump inlet 52 and outlet 60 are both maintained in opened condition.

Operation of the pump is in accordance with U.S. Pat. No. 4,639,245, to Pastrone et al., the disclosure of which is hereby incorporated by reference. Essentially, liquid flow is effected by reciprocation of pump plunger 48 in timed relation to operation of inlet and outlet actuators 28 and 34. A reversible stepping motor, acting through a suitable threaded connection, provides reciprocable stroking of the pump plunger for alternately deforming and relaxing the diaphragm portion 46, thus effecting positive displacement of liquid in the pump chamber 44. During extension of the plunger, for effecting positive liquid flow, outlet actuator 34 is retracted so as to open the liquid outlet 24, while the selected inlet actuator 28 closes the selected liquid inlet 22, 23. Conversely, the liquid outlet 24 is closed, and the selected liquid inlet 22, 23 is opened during retraction of the pump plunger 48, whereby retraction of the pump diaphragm portion 46 effects filling of the pump chamber via the liquid inlet and the flow path 26.

As will be appreciated, the pump 42 can readily be reversibly operated to provide reverse liquid flow in flow path 26. This merely entails reversing the above-described operation of the selected upstream and downstream valve mechanisms so liquid flows in a reverse direction through the pump 42. As will be further described, this technique is employed for effecting reverse fluid flushing in the cassette by introduction of flush liquid into a flush fluid inlet downstream of outlet 24.

Because the pump chamber 44 and pump diaphragm portion 46 together define a predetermined volume and maximum possible displacement for the liquid pump 42, precise control of pump plunger 48 permits precise control of liquid flow through the cassette, thus particularly facilitating accurate and consistent preparation of parenteral solutions. To this end, the pump cassette has been particularly configured to maintain consistent displacement for the pump 42, and to assure consistency of operation from one disposable pump cassette 10 to another.

Consistent displacement of the pump is facilitated by the manner in which the pump diaphragm portion 46 is securely held in position relative to the pump chamber 44 by a pair of cooperating clamping ribs 68 and 70 (FIG. 3) respectively provided on the front and rear body members 16 and 18 of the cassette body. The clamping ribs 68 on the front body member are positioned about the pump chamber 44 (outwardly of the continuous wall portions 16' that extend along and define the flow path 26), with the clamping ribs 68 and 70 positioned in generally confronting relationship to each other on respective opposite sides of the pump diaphragm portion 46 at the pump chamber 44 for enhanced clamping of the diaphragm. The clamping ribs 70 on the rear body member preferably respectively fit within a pair of grooves 71 defined by diaphragm portion 46 for enhanced grip and securement. This preferred arrangement provides a double clamp on the diaphragm, thereby effecting a very secure and stable gripping force on the diaphragm to act to preclude any possible shifting of the diaphragm relative to the pump chamber, which could otherwise affect the effective displacement of the pump.

Further pumping consistency is achieved, from one disposable cassette to another, by the illustrated arrangement wherein the front body member 16 defines the pump chamber 44 and associated liquid flow path 26 and valve seats.

Specifically, the front body member 16 further includes an arrangement for positively and consistently positioning the front body member, and thus the pump chamber 44 defined thereby, in the desired predetermined relationship relative to the pump drive, and in particular, relative to pump plunger 48. In the illustrated embodiment, this positioning arrangement is provided by a positioning opening 72 defined by the pump cassette 10, with the positioning opening 72 configured to receive a cassette positioning member 74 of the pump driver 12.

In the preferred embodiment, another positioning opening 73 is provided, and similarly receives another positioning member 75 of the pump driver 12. Notably, the internal peripheral surface 76 of the positioning opening 72 is provided by the front body member 16, with this peripheral surface being positioned for engagement with the cassette positioning member 74 when it is received within positioning opening 72. The internal peripheral surface 77 of opening 73 is likewise provided by the front body member for engagement with its respective positioning member 75. As will be appreciated, this preferred configuration acts to provide the desired predetermined positioning between the pump chamber 44 and the associated pump plunger 48, and between the various valve actuators and associated valve seats for consistent and positive flow control.

Further preferred features of the present pump cassette and pump driver facilitate automatic and air-free compounding of admixture solutions. In order to identify an absence of source solution or other liquid flowing into the pump cassette 10 via one of the inlets 22 and 23, an air detection arrangement is provided in fluid communication with the liquid flow path 26 downstream of the liquid inlets 22. Specifically, the diaphragm 20 includes an air detection portion 78 which projects rearwardly through the rear body member 18, and within which is received a projection 80 formed on front body member 16. Together, the diaphragm portion 78 and projection 80 form a portion of the liquid flow path 26 which extends rearwardly from the rear body member 18, and thus is positioned to be received within a air detector 82 of the pump driver 12. The diaphragm 20 is preferably formed from a translucent, silicon-based elastomer, with the air detector 82 preferably configured to optically detect the presence of air (and thus the absence of liquid) in the diaphragm portion 78. As illustrated, a pair of guards 83 are preferably formed on the rear body member 18 to protect and shield the diaphragm portion 78.

In the preferred embodiment, the present system further includes a pressure transducing arrangement for sensing and monitoring pressure within the pump cassette 10, thus detecting proximate or distal occlusion of the system. The pressure transducing arrangement includes a pressure sensor cavity 84 defined by front body member 16, and a diaphragm portion 86 which fits across the cavity 84. A sensor opening 88 is defined by the rear body member 18 in alignment with diaphragm portion 86, with the pump driver 12 including a pressure transducing device having a sensor rod 90 which fits through the opening 88 to contact diaphragm portion 86.

During normal pump operation, liquid pressure within cavity 84 is represented by a wave-form function with consistent peaks for each full, positive liquid displacement. Such consistency is also exhibited from one pump cassette to another. However, fluctuation in peak pressure may indicate occlusion or other malfunctions in the system. An increase in the sensed pressure is ordinarily associated with occlusion or other liquid flow blockage downstream of the sensor cavity 84. In contrast, a lowering in the sensed pressure indicates the possibility of occlusion upstream of the sensor cavity 84. As will be appreciated, the provision of this pressure transducing arrangement facilitates convenient and consistent testing of each disposable pump cassette for correct function.

Figure 6:
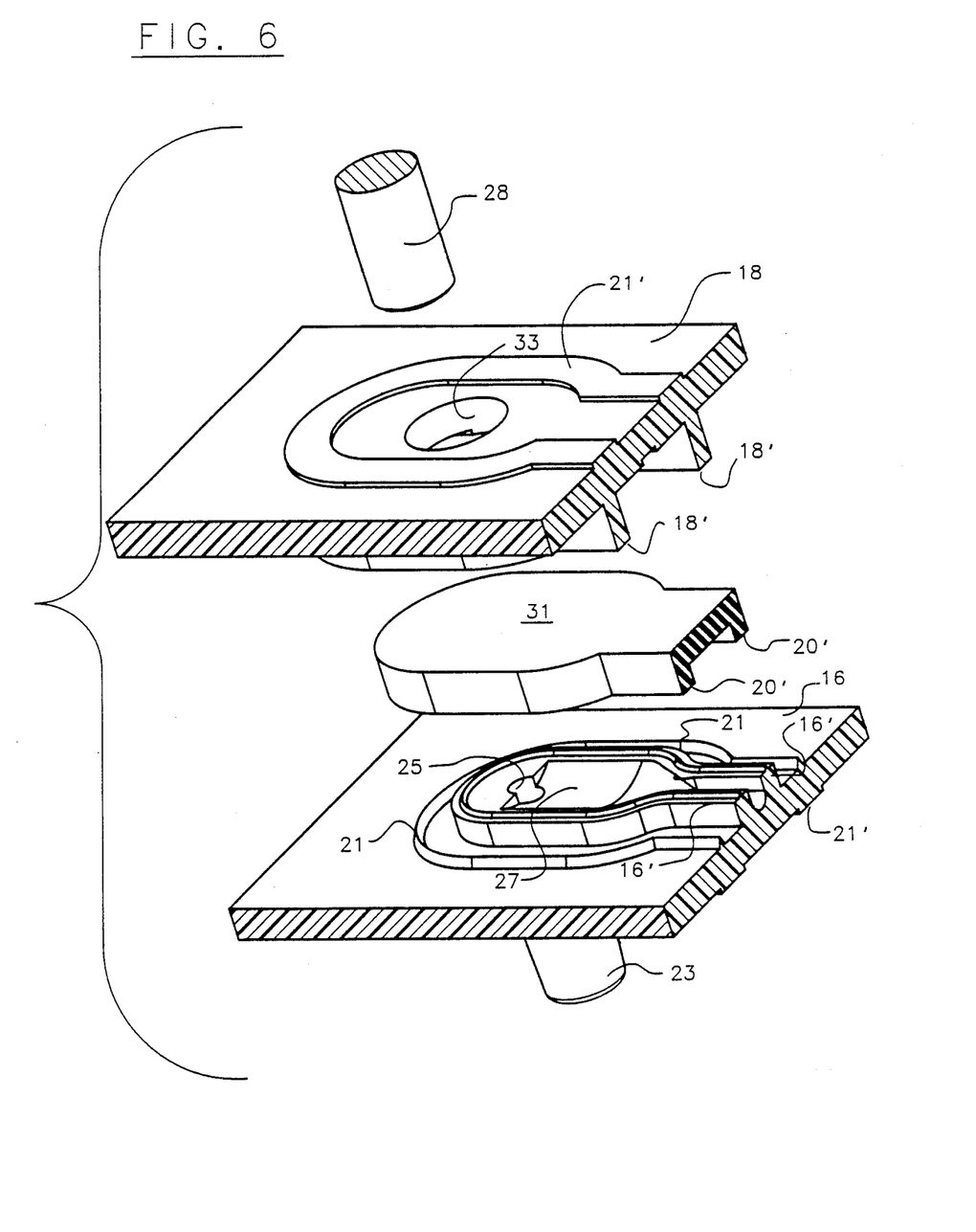
FIG. 6 is an exploded perspective view of a valve mechanism of the pump cassette of the present system.

Upon completion of preparation of a given admixture solution, it is normally desirable to flush the interior of the pump cassette 10, including the liquid pump 42 and the flow path 26, with flush liquid, typically sterile water. To facilitate such flushing, a flush fluid inlet 92 (preferably configured similarly to upstream most inlet 23, as shown in FIG. 6) is provided in the front body member 16, with the flush fluid inlet 92 disposed in fluid communication with the liquid flow path 26 downstream of liquid outlet 24. By the provision of flush fluid inlet 92, priming and/or flushing liquid can be introduced into the pump cassette via tubing F from flush fluid container W, and flowed therethrough in a direction opposite that of the normal direction of liquid flow in the liquid flow path 26. To this end, the upstream most one of liquid inlets 23, shown at the upstream end of flow path 26, is intended to function as the outlet for such priming and/or flushing fluid.

As in the case of other liquid inlet and outlet constructions of the pump cassette 10, the flush inlet 92 is configured for selective operation by an inlet actuator 94 of pump driver 12. A diaphragm portion 96 coacts with the flush inlet 92 under the influence of the actuator 94, which acts against the diaphragm portion 96 through a flush inlet opening 98 defined by rear body member 18.

Reverse fluid flow for flushing is effected by operating pump 42, in timed relation to operation of flush inlet actuator 94 and the inlet actuator 28 for upstream most inlet 23. Thus, the flush fluid inlet 92 and the inlet 23 (functioning as an outlet) are alternately opened and closed.

In order to monitor the presence or absence of flush fluid in the cassette flow path, another air detection arrangement is preferably provided, in this case in fluid communication with the flush fluid inlet 92. As illustrated, a diaphragm portion 100 projects through the rear body member 18, and together with a projection 102 on the front body member 16 which is received within the diaphragm portion 100, defines a flow path extending from the rear body member 18. The diaphragm portion 100 is configured for cooperation with an associated air detector 104 of the pump drive 12, with this arrangement thus being configured to detect the absence of flush fluid in the flow path. A pair of guards 105 are preferably provided on the rear body member 18 to protect the diaphragm portion 100.

As discussed, the present solution pumping system is particularly configured for compounding parenteral admixture solutions. In this regard, the preparation of small volume parenteral solutions typically entails the introduction of predetermined quantities of source solutions into the parenteral solution container, with such source solutions typically comprising drugs and like therapeutic agents. This is to be distinguished from preparation of large volume parenteral solutions (which are typically nutritional rather than therapeutic in nature), since preparation of such small volume solutions ordinarily requires compounding of source solutions of drugs and like therapeutic agents in a relatively concentrated and undiluted form.

As such, it is desirable to avoid inadvertent mixing of these relatively concentrated source solutions so as to avoid the inadvertent mixing of incompatible drugs, which can result in formation of precipitate. To this end, the present pump cassette 10 has been particularly configured at each of its liquid inlets 22 (but not at the upstream most inlet 23), so that liquid flow between upstream and downstream portions of the liquid flow path at each of these downstream ones of said inlets flushes residual liquid from the region thereof. This avoids mixture of incompatible liquids in the cassette, thereby precluding possible formation of precipitate or like reaction.

Figure 7:
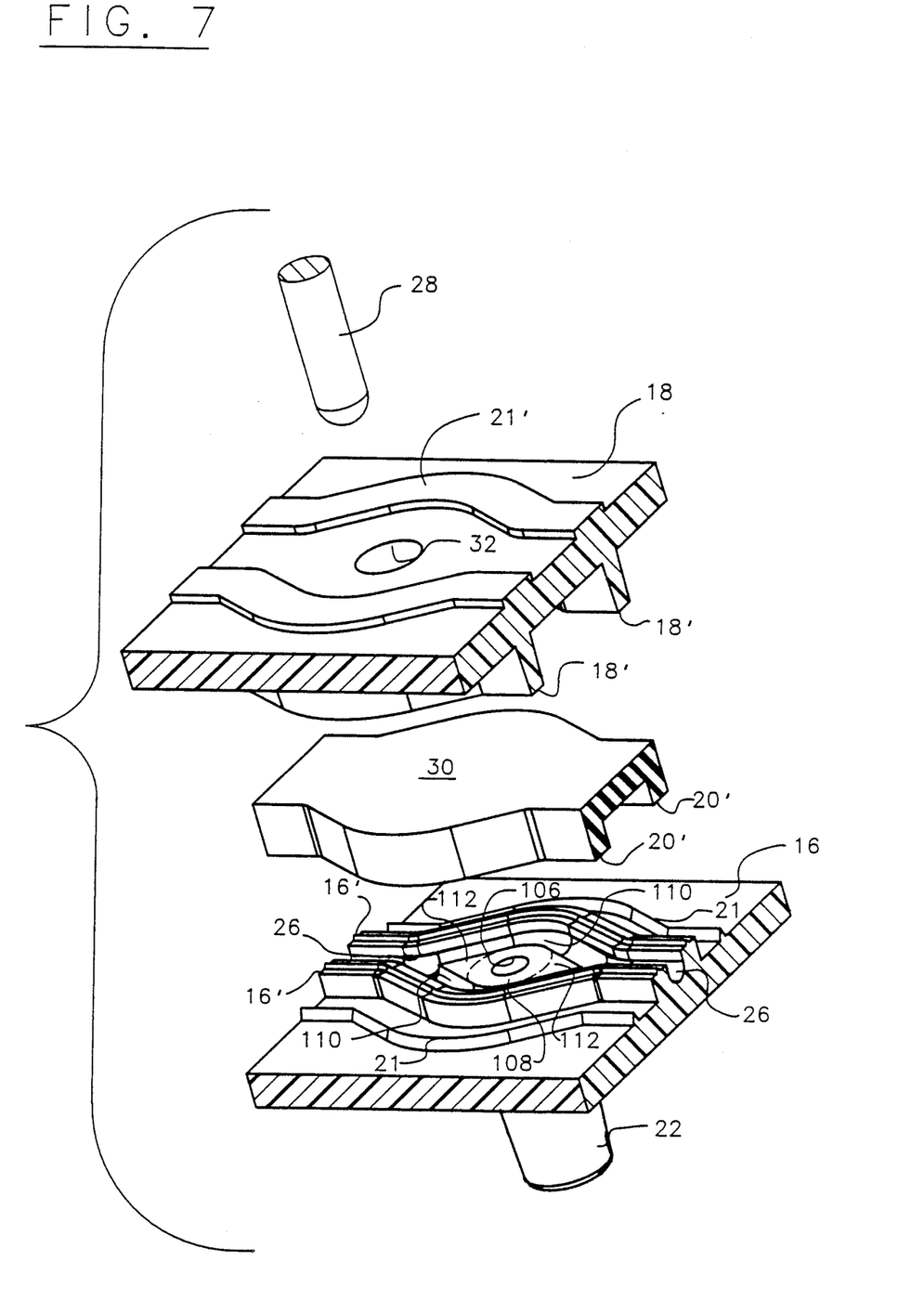
FIG. 7 is an exploded perspective view of a valve mechanism, including a liquid flushing arrangement, of the pump cassette of the present system.

To this end, and with reference to FIG. 7, each of the aforementioned liquid inlets 22 comprises a liquid inlet passage 106 defined by the front body member 16, with each liquid passage 106 terminating in a peripheral valve seat 108 (generally within the phantom lines shown in FIG. 7). As noted, each inlet diaphragm portion 30 cooperates with a respective one of the peripheral valve seats 108 (under the influence of the respective inlet valve actuator 28) to effect selective opening and closing of the inlet for controlling liquid flow therethrough.

At each of the inlets 22 arranged between upstream and downstream portions of liquid flow path 26, a liquid flushing arrangement is provided in the form of at least one bypass passage 110 of the liquid flow path 26. Each bypass passage 110 extends adjacent to the respective peripheral valve seat 108, and thus is arranged for flushing residual liquid from the region of the respective liquid inlet 22.

In the illustrated, preferred form, the desired liquid flushing is effected by the provision of a pair of the bypass passages 110 extending on respective opposite sides of the peripheral valve seat 108 at the respective liquid inlet 22. In the particularly preferred form, streamlined liquid flow past the peripheral valve seat 108 is facilitated by the provision of a pair of streamlining lands 112 positioned on respective upstream and downstream sides of the valve seat 108 between the pair of bypass passages 110.

As will be appreciated, this preferred liquid flushing arrangement can be operated to effect flushing of residual liquid from a previously open inlet by the introduction of liquid across the one inlet, such as by introduction through flush fluid inlet 92. In this regard, flushing fluid in the form of sterile water or the like may be employed. A particularly preferred technique for effecting a flushing-like action concerns use of the parenteral admixture solution which is being prepared by recirculation of the admixture into the upstream most inlet 23, thus desirably avoiding dilution of the admixture solution with a neutral flushing fluid. Copending patent application Ser. No. 07/444,487, filed Dec. 1, 1989, discloses a particularly preferred method for effecting recirculation of the admixture solution.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. A pump cassette for use with an associated pump driver having a reciprocable pump plunger and a plurality of valve actuators, said pump cassette comprising:
   a cassette body including a plate-like front body member, and a juxtaposed, plate-like rear body member; and
   elastomeric diaphragm means positioned between said front and rear body members, said cassette body and said diaphragm means together providing said pump cassette with a plurality of liquid inlets including at least one downstream inlet at least one liquid outlet, a liquid flow path for joining said liquid inlets and outlet in fluid communication, and pump means operably driven by the pump plunger of said associated pump driver for pumping liquid from a selected one of said liquid inlets to said liquid outlet via said flow path,
   said front and rear body members being joined to each other at marginal joint means extending along at least a portion of confronting marginal edges of said front and rear body members,
   said front and rear body members being further joined together inwardly of said marginal joint means at diaphragm joint means, said diaphragm joint means extending completely about the periphery of said diaphragm means for enhancing sealing of said liquid flow path.

2. A pump cassette in accordance with claim 1, wherein
   said cassette body and said diaphragm means together provide at least one downstream one of said liquid inlets with liquid flushing means, so that liquid flow between upstream and downstream portions of said flow path at said one of said inlets flushes residual liquid from the region of said one inlet, thereby avoiding mixture of incompatible liquids in said cassette.

3. A pump cassette in accordance with claim 2, including
   air detection means projecting generally outwardly from said cassette body and disposed in fluid communication with said flow path downstream of said liquid inlets,
   said air detection means being configured for cooperation with an associated air detector of said pump driver for detecting the presence of air in said liquid flow path.

4. A pump cassette in accordance with claim 2, including
   a flush fluid inlet disposed in fluid communication with said flow path downstream of said liquid outlet for introducing flushing liquid into the flow path of said pump cassette, and air detection means projecting generally outwardly from said cassette body and disposed in fluid communication with said flush fluid inlet, and said air detection means being configured for cooperation with an associated air detector of said pump driver for detecting the absence of flush fluid in said flow path.

5. A pump cassette in accordance with claim 1, wherein
   said front body member defines a pump chamber which provides said pump means together with said elastomeric diaphragm means, said front body member further defining clamping rib means positioned about said pump chamber for engagement with said diaphragm means,
   said rear body member defining another clamping rib means engageable with said diaphragm means, said clamping rib means of each of said front and rear body members positioned in generally confronting relationship to each other on respective opposite sides of said diaphragm means at said pump chamber for enhanced clamping of said diaphragm means.

6. A pump cassette in accordance with claim 1, wherein said liquid flow path includes a generally U-shaped portion having a pair of legs, each of said legs having a plurality of said liquid inlets positioned therealong.

7. A pump cassette for use with an associated pump driver having a reciprocable pump plunger and a plurality of valve actuators, said pump cassette comprising:

a rigid cassette body; and elastomeric diaphragm means positioned in said cassette body, said cassette body and said diaphragm means together providing said pump cassette with a plurality of liquid inlets, at least one liquid outlet, a liquid flow path for joining said liquid inlets and outlet in fluid communication, and pump means operably driven by the pump plunger of said associated pump driver for pumping liquid from a selected one of said liquid inlets to said liquid outlet via said flow path, said cassette body and said diaphragm means together providing at least one downstream one of said liquid inlets with liquid flushing means so that liquid flow between upstream and downstream portions of said flow path at said one inlet flushes residual liquid from the region of said one liquid inlet, thereby avoiding mixture of incompatible liquids in said cassette.

8. A pump cassette in accordance with claim 7, wherein said one of said liquid inlets comprises an inlet passage defined by said cassette body and terminating in a peripheral valve seat, said diaphragm means being engageable with said valve seat by operation of one of said valve actuators of said associated pump driver for controlling liquid flow through said one inlet, and said liquid flushing means comprises at least one bypass passage means of said liquid flow path of said cassette, said bypass passage means extending adjacent to said peripheral valve seat for flushing residual liquid from the region of said one liquid inlet.

9. A pump cassette in accordance with claim 8, wherein said liquid flushing means comprises a pair of said bypass passage means extending on respective opposite sides of said peripheral valve seat of said one liquid inlet.

10. A pump cassette in accordance with claim 9, including means for streamlining liquid flow past said peripheral valve seat and through said pair of bypass passage means, said streamlining means comprising a pair of streamlining lands positioned on respective upstream and downstream sides of said valve seat and between said pair of bypass passage means.

11. A pump cassette in accordance with claim 8, wherein said cassette body and said diaphragm means together providing a plurality of said liquid inlets with respective ones of said liquid flushing means.

12. A pump cassette in accordance with claim 7, wherein said cassette body comprises a front body member, and a juxtaposed rear body member, between which is positioned said elastomeric diaphragm means, said front body member defining said liquid flow path together with said diaphragm means, and further defining a pump chamber of said pump means with said diaphragm means, said front body member further comprising cassette positioning means engageable with an associated cassette positioning member of said pump drive to thereby facilitate accurate positioning of said pump chamber relative to said associated pump plunger of said pump drive.

13. A pump cassette in accordance with claim 12, wherein said cassette body defines a positioning opening within which said associated positioning member is received, said cassette positioning means of said front body member comprising the peripheral surface of said positioning opening for engagement with said associated positioning member.

14. A pump cassette in accordance with claim 7, wherein said cassette body comprises a front body member, and a juxtaposed rear body member between which is positioned said elastomeric diaphragm means, said front and rear body members being joined to each other at marginal joint means extending along at least a portion of confronting marginal edges of said front and rear body members, said front and rear body members being further joined together inwardly of said marginal joint means at diaphragm joint means, said diaphragm joint means extending completely about the periphery of said diaphragm means for enhancing sealing of said liquid flow path.

15. A pump cassette in accordance with claim 14, wherein said marginal joint means and said diaphragm joint comprising sonic welding.

16. A solution pumping system, comprising a pump driver, said pump driver including a reciprocable pump plunger, and a plurality of valve actuators; and a pump cassette removably positionable in operative association with said pump driver, said pump cassette including a cassette body comprising a front body member and a juxtaposed rear body member, and an elastomeric diaphragm positioned between said front and rear body members, said front body member defining together with said diaphragm a plurality of liquid inlets, at least one liquid outlet, a liquid flow path for joining said liquid inlets and outlet in fluid communication, and pump means operably driven by the pump plunger of said associated pump driver for pumping liquid from a selected one of said liquid inlets to said liquid outlet via said flow path, each of said inlets and outlets comprising a liquid passage defined by said front body member and terminating in a valve seat, said rear body member defining a plunger opening at said pump means for operative engagement of said reciprocable pump plunger with said diaphragm means for operating said pump means, said rear body member further defining a plurality of valve actuator openings at respective ones of said liquid inlets and outlets for operative engagement of respective ones of said valve actuators with said diaphragm for selectively urging said diaphragm against said valve seats of said inlets and outlets for selecting controlling liquid flow therethrough, said front body member and said diaphragm together providing a plurality of downstream ones of said liquid inlets with liquid flushing means so that liquid flow between upstream and downstream portions of said flow path at each of said ones of said liquid inlets flushes residual liquid from the region of the liquid inlet, thereby avoiding mixture of incompatible liquids in said cassette, each of said liquid flushing means comprising at least one bypass passage means of said liquid flow path extending adjacent to the valve seal of the respective one of said liquid inlets.

17. A solution pumping system in accordance with claim 16, wherein said pump driver includes at least one cassette positioning member, said cassette body defining a positioning opening within which said positioning member is received when said pump cassette is positioned in operative association with said pump driver, said front body member defining the peripheral surface of said positioning opening for engagement with said positioning member to facilitate accurate positioning of said pump chamber relative to said reciprocable pump plunger.

18. A solution pumping system in accordance with claim 17, wherein said front body member defines a pump chamber which provides said pump means together with said elastomeric diaphragm means, said front body member further defining clamping rib means positioned about said pump chamber for engagement with said diaphragm means, said rear body member defining another clamping rib means engageable with said diaphragm means, said clamping rib means of each of said front and rear body members positioned in generally confronting relationship to each other on respective opposite sides of said diaphragm means at said pump chamber for enhanced clamping of said diaphragm means.

19. A solution pumping system in accordance with claim 18, wherein said front and rear cassette body members are joined to each other at marginal joint means extending along at least a portion of confronting marginal edges of said front and rear body members, said front and rear body members being further joined together inwardly of said marginal joint means at diaphragm joint means, said diaphragm joint means extending completely about the periphery of said diaphragm means for enhancing sealing of said liquid flow path.

20. A pump cassette in accordance with claim 19, wherein said marginal joint means and said diaphragm joint each comprise sonic welding.

21. A solution pumping system in accordance with claim 16, wherein said pump cassette includes air detection means projecting generally outwardly from said cassette body and disposed in fluid communication with said flow path downstream of said liquid inlets, said pump driver including an air detector configured for cooperation with said air detection means for detecting the presence of air in said liquid flow path.

22. A pump cassette in accordance with claim 16, wherein said pump cassette includes a flush fluid inlet disposed in fluid communication with said flow path downstream of said liquid outlet for introducing flushing liquid into the flow path of said pump cassette, and air detection means projecting generally outwardly from said cassette body and disposed in fluid communication with said flush fluid inlet, said pump driver including air an detector configured for cooperation with said detection means for detecting the absence of flush fluid in said flow path.

* * * * *